United States Patent [19]

Schoendorfer

[11] Patent Number: 4,850,998
[45] Date of Patent: Jul. 25, 1989

[54] METHOD FOR WETTING A PLASMAPHERESIS FILTER WITH ANTICOAGULANT

[75] Inventor: Donald W. Schoendorfer, Santa Ana, Calif.

[73] Assignee: Baxter International Inc., Deerfield, Ill.

[21] Appl. No.: 106,089

[22] Filed: Oct. 7, 1987

[51] Int. Cl.⁴ ............................................ A61M 1/00
[52] U.S. Cl. .................................... 604/28; 210/139; 604/6
[58] Field of Search ....................................... 604/4–6, 604/28; 210/139, 651, 321.84

[56] References Cited

U.S. PATENT DOCUMENTS

| | | |
|---|---|---|
| 4,191,182 | 3/1980 | Popovich et al. ...................... 604/6 |
| 4,578,056 | 3/1986 | King et al. ............................... 604/6 |
| 4,605,503 | 8/1986 | Bilstad et al. ........................... 604/6 |
| 4,648,866 | 3/1987 | Malbrancq et al. ..................... 604/6 |
| 4,657,529 | 4/1987 | Prince et al. ................. 128/DIG. 13 |

FOREIGN PATENT DOCUMENTS 8102979  10/1981  PCT Int'l Appl. ..................... 604/6

Primary Examiner—John D. Yasko
Assistant Examiner—Mario Costantino
Attorney, Agent, or Firm—Paul C. Flattery; Bradford R. L. Price; Richard G. Besha

[57] ABSTRACT

A method of wetting a plasmapheresis filter with anticoagulant in a plasmapheresis system having a venepuncture needle, a plasma separation device connected in series by a fluid conduit, including operating the system such that an initial limited volume charge of anticoagulant is introduced into the conduit (for wetting the filter of the separation device) in advance of whole blood flowing from the donor towards to the separation device (and pushing the anticoagulant charge ahead of the whole blood into the separation device).

17 Claims, 2 Drawing Sheets

METHOD FOR WETTING A PLASMAPHERESIS FILTER WITH ANTICOAGULANT

BACKGROUND OF THE INVENTION

The present invention relates generally to a method for operating a system for separating constituents of blood and particularly relates to a method of wetting the plasmapheresis filter of a plasma/cell concentrate separation device with anticoagulant.

There are a number of automated, on-line donor, plasmapheresis systems for the separation of whole blood into two or more of its constituents including, for example, plasma and blood cell concentrate. Such systems are designed to collect a predetermined volume of plasma from a donor using a fully automated processing program in conjunction with a plasmapheresis instrument and a disposable tubing set or harness packaged separately from the instrument. One such system is the Autopheresis-C Plasmapheresis System manufactured by Baxter Healthcare Corporation, a wholly-owned subsidiary of the assignee of the present invention.

In that system, a microprocessor controls a number of pumps, clamps, detectors, monitoring systems, etc., for automating the collection of whole blood from the donor, separating the blood into plasma and cell concentrate, collecting the plasma and reinfusing the cell concentrate to the donor using a disposable tubing set or harness installed in the instrument. Generally, the tubing set includes a venous phlebotomy needle for whole blood collection and blood concentrate reinfusion, a separator for separating anticoagulated whole blood into plasma and cell concentrate, a plasma collection container for receiving the plasma from the separator, a reinfusion reservoir from which cell concentrate flows back to the donor during reinfusion and a length of tubing runs for connection with other parts of the instrument and its various pumps, clamps and detectors. Thus, upon installation of the tubing set in the instrument and various setup procedures, the instrument operates to alternate between collection and reinfusion cycles. In the collection cycle, anticoagulated whole blood is pumped by a blood pump to the separator of the tubing set where it is separated into plasma which flows to a collection container and cell concentrate which flows to the reinfusion reservoir. In the reinfusion cycle, the blood pump reverses to flow cell concentrate from the reservoir through the phlebotomy needle to the donor.

More particularly, in the above-described system, a hydrophilic filter is used to effect the separation of the plasma and cell concentrate in the separation device. In using such separation device, it has been found necessary to wet its filter before it comes into contact with the whole blood. The degree of this effect depends greatly on the composition of the filter. For instance, nylon requires prior wetting; polycarbonate does not. If the nylon filter is not first wetted before blood contact, the first plasma that penetrates the filter can contain an undesirably high concentration of hemoglobin. Without wetting, the transfilter pressure required to displace this first plasma portion across the filter is also quite high and much higher than if the filter is already been wetted. It is also believed that this initial high transfilter pressure contributes to a certain degree of plugging of the filter which results in lower plasma flows and which plugging and lower plasma flows do not occur if the filter is initially wetted. Because saline solution was used in the system for other purposes, such system has, in the past, been modified to initially wet the filter with saline. This is accomplished during initial setup of the tubing and prior to any blood collection from the donor. By wetting the separation filter with saline, hemolysis of the first plasma portion through the filter is avoided. Additionally, the large buildup of transfilter pressure and the subsequent more rapid plugging of the filter are similarly avoided.

Recently, however, interest has been demonstrated in plasmapheresis with protocols that do not require saline. Consequently, it is intended to modify a conventional plasmapheresis system to eliminate the mechanisms and procedures for the introduction of saline into the tubing harness except with respect to the emergency administration of saline if required. However, the requirement to wet the filter to avoid hemolysis of the first plasma portion, as well as to retain the other advantages of wetting mentioned above, remain.

Because the only aqueous solution left in the system is anticoagulant, it was initially believed that anticoagulant could be used to wet the filter through the previously used saline line. That is, two asceptic spike penetrations into the anticoagulant bag would be provided, one with the normal anticoagulant spike and the other with the existing saline spike. There is danger, however, in that it is possible for the existing saline spike line to come out of its clamp and thus have anticoagulant administered in an uncontrolled manner to the donor. This is dangerous because anticoagulant generally is composed of citrate which chemically binds to calcium in the donor's body. Too much citrate binds too much calcium, which can cause physiological effects in the donor from mild paraesthesia to cardiac arrest, depending on the quantities involved.

Another proposed solution was to wet the filter of the separation device with anticoagulant through the anticoagulant line in the blood tubing and directly onwards to the separation device in a manner similar to that used in the part with saline solutions. It was found, however, that a substantial quantity about (e.g., 25 ml) of anticoagulant was necessary in order to initially reach the separation device and thereby to initially wet the filter. Because that initial quantity of anticoagulant would have to be returned to the donor at the end of the first collection cycle, there was the undesirable potential for citrate reactions by the donor. Consequently, there was the need for a method of wetting the filter of the separation device in a manner which would avoid hemolysis of the plasma, initial build-up of transfilter pressure and later plugging of the filter, yet which would have no adverse effects on the donor and would minimally impact the current system setup.

Now, however, we have discovered a way to successfully use available anticoagulant for pre-wetting the filter while yet avoiding all the above-mentioned possible disadvantages. Only a limited volume of anticoagulant is passed into a blood supply conduit in advance of the blood. Thus, as the blood later initially passes through the conduit, it pushes ahead of it the limited volume anticoagulant charge thereby to pre-wet the filter as it initially passes into the downstream separation device.

According to the present invention, there is provided a method for wetting the filter of the separation device with anticoagulant. To accomplish this, the tubing harness is applied to the instrument as before. However, only a small amount (e.g., about 6–7 ml) of anticoagulant is first primed into the system. Thus, the blood line clamp is closed, the reinfusion line clamp is open and the anticoagulant pump and blood pump are operated to supply anticoagulant from the anticoagulant supply past its Y-connection with the blood line sufficiently such that there is only a small charge of anticoagulant in the blood line in advance of any whole blood entering the system after venepuncture. This anticoagulant prime continues until a predetermined quantity or charge of anticoagulant is supplied to the blood line and detected in the blood line, preferably by the system air detector. The air detector then signals the microprocessor to stop the anticoagulant prime in the blood line, preferably such that the blood line may contain a small additional quantity of anticoagulant beyond the air detector. Once stopped, various conventional procedures are performed by the instrument in setting up for blood collection and reinfusion with respect to a particular donor.

After such setup and following venepuncture performed on the donor, the blood line clamp between the plasma separation device and the blood pump is opened and the reinfusion line clamp between the reinfusion reservoir and the blood line is closed. This initially supplied limited charge of anticoagulant is then pumped by the blood pump through the blood line so as to advance (prior to the incoming blood supply) into the separation device so as to pre-wet the filter. It will be appreciated that anticoagulated whole blood follows behind this leading charge of anticoagulant in the blood line and forms a whole blood/anticoagulant charge interface. Sufficient blood is pumped such that the initial charge of anticoagulant reaches and wets the filter. This may be detected by, for example, counting a predetermined number of turns of the blood pump and providing a signal in response thereto. The tubing runs are such that the signal indicates that sufficient anticoagulated whole blood has been pumped to enable the initial anticoagulant charge to reach the separation device and wet the filter (before any blood reaches the filter). That detection signal enables the instrument to proceed to the next step, e.g., to prime the reinfusion reservoir with whole blood. Thus, after the filter of the separation device is wetted, the blood line clamp is closed and the reinfusion line clamp is opened and the blood line pump is operated to flow anticoagulated whole blood into the bottom of the reinfusion reservoir. Once this priming is complete, the reinfusion line clamp is closed and the blood line clamp is opened, thereby initiating the first collection cycle. By using this sequence of operation, the fluid first flowing into the separation device constitutes the initial anticoagulant filter wetting charge, followed immediately by anticoagulated whole blood.

According to a preferred embodiment of the present invention, there is provided a method of wetting a plasmapheresis filter with anticoagulant in a plasmapheresis system having a venepuncture needle and a plasma separation device connected by a fluid conduit comprising the steps of providing the conduit with a predetermined amount of anticoagulant, performing the venepuncture to provide the conduit with whole blood from a donor, and pumping the whole blood in the conduit such that a limited volume of anticoagulant in the conduit is provided to the separation device first and in advance of whole blood to wet the plasmapheresis filter before substantial contact with whole blood. Preferably, only a small predetermined amount of anticoagulant is received in the reservoir, for example, on the order of 3 to 4 ml, and preferably no more than about 5 ml as a result of initially wetting the filter with anticoagulant in accordance with this invention. This small amount of anticoagulant returned to the donor at the end of the first cycle has no clinical physiological significance.

Accordingly, it is a primary object of the present invention to provide a novel and improved method for wetting the plasmapheresis filter of a blood separation device with anticoagulant in a manner to achieve the beneficial purposes of initially wetting the filter, i.e., avoiding hemolysis of initial plasma portions, large buildup in transfilter pressure and later plugging of the filter, and without adverse effect on the donor when this wetting charge of anticoagulant is subsequently infused back into the donor.

These and further objects and advantages of the present invention will become more apparent upon reference to the following specification, appended drawings and claims.

BRIEF DESCRIPTION OF THE DRAWING FIGURES

FIG. 1 is a schematic flow diagram for a plasmapheresis system wherein anticoagulant is used to wet the plasmapheresis filter of a separation device in accordance with the present invention; and FIG. 2 is a block diagram illustrating the stage of operation of the system hereof.

DETAILED DESCRIPTION OF THE DRAWING FIGURE

Figure 1:
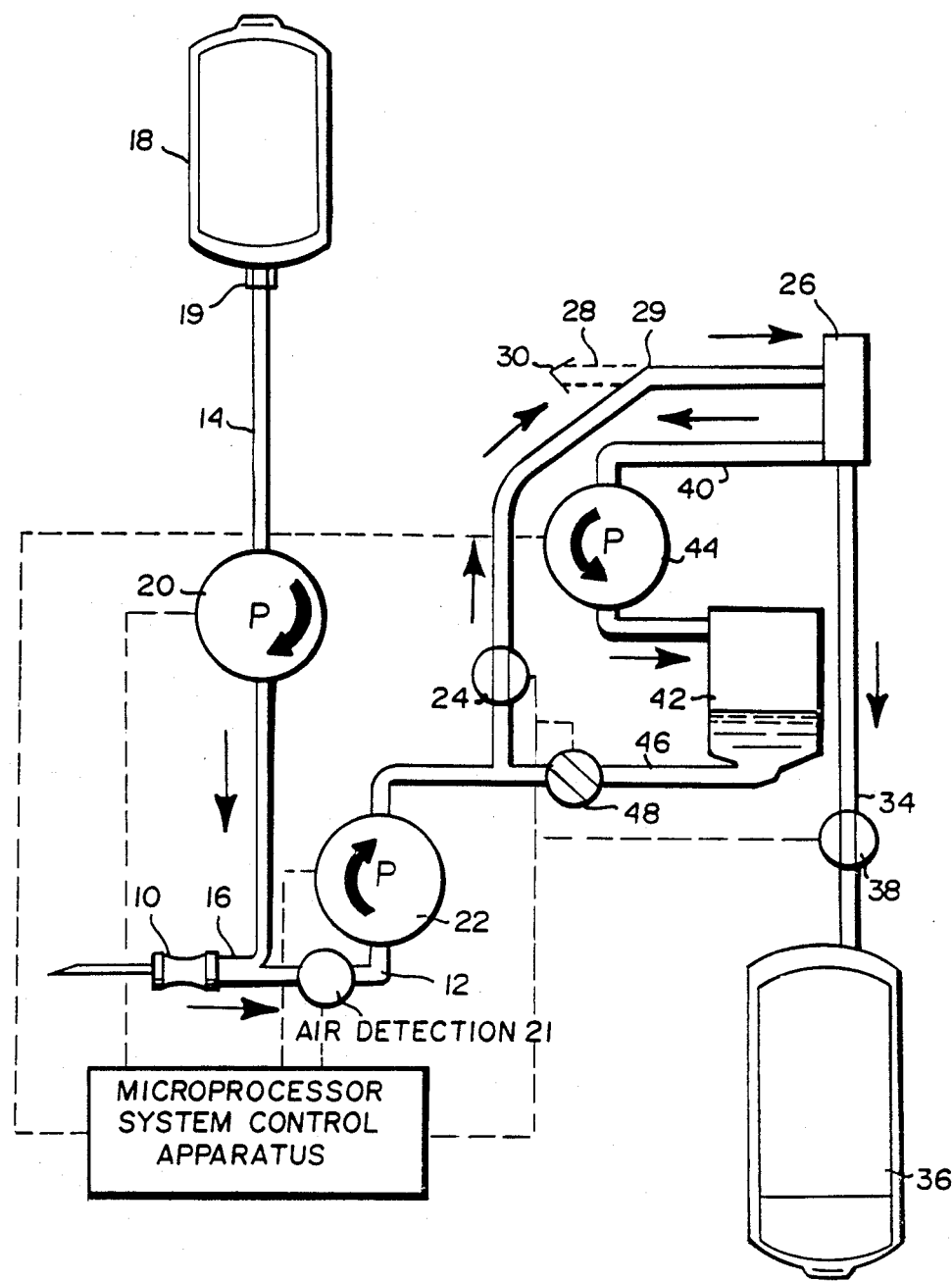

Referring now to FIG. 1, there is illustrated a plasmapheresis system for use in practicing the method of the present invention. In this system, there is provided a venepuncture needle set 10 for receiving whole blood from the donor and reinfusing cell concentrate into the donor. Venepuncture needle set 10 communicates with a blood line 12. An anticoagulant line tubing 14 communicates with blood line 12 adjacent the venepuncture needle set 10 through a Y-connection 16 and, at its opposite end, with a nipple 19 formed on an anticoagulant supply bag 18. An anticoagulant peristaltic pump 20 pumps anticoagulant from the supply 18 to the Y-connection 16 for introduction into blood line 12.

Blood line 12 is connected through an air detector 21, a peristaltic blood pump 22 and a blood line clamp 24 with a plasma separation device 26. The plasma separation device may be of conventional construction, for example, the disposable plasma separator device denoted Plasmacell-C manufactured by Baxter Healthcare Corporation. That separator includes a filter formed on nylon material, although it will be appreciated that other types of filter materials may be used.

By means of a filter within the separation device 26, whole blood is separated into constituents comprising plasma and cell concentrate. The plasma flows from the separation device 26 through a plasma line 34 and a plasma line clamp 38 to a plasma collection container or bag 36. The cell concentrate flows through a line 40 into a reinfusion reservoir 42, the line 40 having a concentrated cell pump 44 for delivering the concentrated cells from separation device 26 to reservoir 42 during the collection cycle. A line 46 connects the lower end of reservoir 42 through a reinfusion line clamp 48 with blood line 12 between blood pump 22 and blood line clamp 24. All of the elements thus far described are conventional elements of the tubing set or the plasmapheresis instrument or ancillary products such as anticoagulant supply bag 18.

Figure 2:
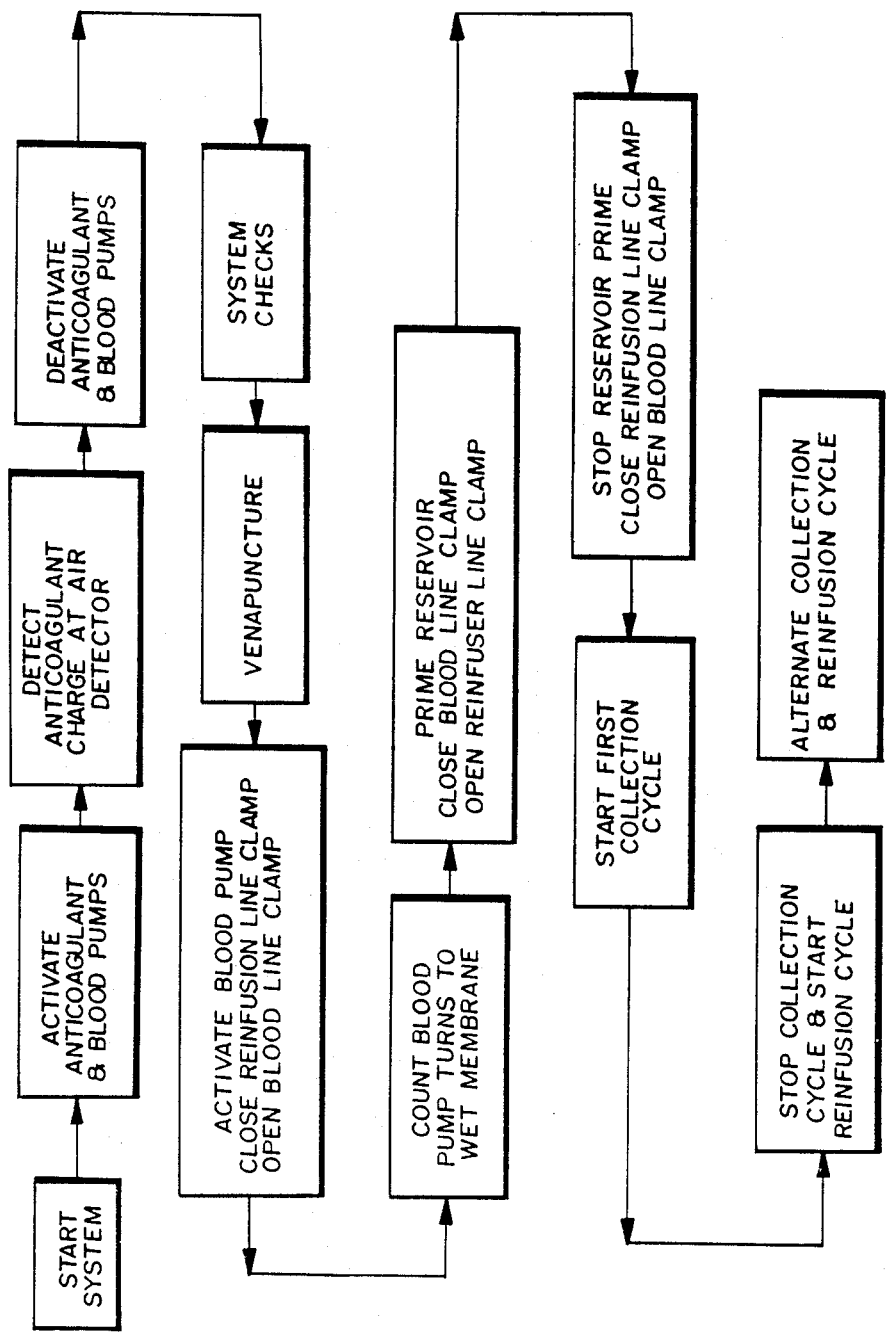

From the foregoing, it will be appreciated that the method of the present invention provides for wetting the plasmapheresis filter of the separation device with anticoagulant rather than saline. To accomplish this and with reference to FIGS. 1 and 2, after the set has been installed in the instrument and prior to venepuncture, the microprocessor instructs the operator to attach the anticoagulant source 18 to the tube 14. The microprocessor system control apparatus activates anticoagulant pump 20 and blood pump 22 to pump from anticoagulant supply 18 through line 14 a predetermined quantity of anticoagulant into blood line 20 past Y-connection 16. Anticoagulant pump 20 and blood pump 22 thus run simultaneously at different rates to flow an initial predetermined quantity or charge of anticoagulant into blood line 20 past air detector 21. Air detector 21 detects this initial charge of anticoagulant fluid in blood line 12 and provides a signal to the microprocessor to stop pumps 20 and 22. Preferably, the pumps are stopped a predetermined time after the signal in order that an additional quantity of anticoagulant is supplied blood line 12 past air detector 21. Consequently, before venepuncture, there is provided in blood line 12 between the phlebotomy needle of the venepuncture needle set 10 and air detector 21 an initial predetermined quantity or charge of anticoagulant.

At this stage, the microprocessor, not shown, then controls the system to perform various functions. For example, once the initial anticoagulant charge is provided blood line 12 for purposes of subsequently wetting the filter of separation device 26, the microprocessor controls the instrument to indicate an anticoagulant/blood ratio, indicate the desired quantity of plasma to be collected, open and close the blood pump to equalize the pressures throughout the system, check the potential for air in the system and various other functions, all prior to connecting the system with the donor.

When the system is ready for the blood line prime which results in wetting the filter with anticoagulant, venepuncture needle set 10 is applied to the donor. Blood line clamp 24 is opened and reinfusion line clamp 48 is closed. Anticoagulated pump 20 and blood pump 22 are restarted. The donor's whole blood is thus pumped by blood pump 22 through blood line 12 toward and into separation device 26, anticoagulant being added thereto through line 14 by pump 20 in a predetermined ratio to the whole blood. It will be appreciated that by this action, the charge of anticoagulant in advance of the anticoagulated whole blood is displaced along line 12 into separation device 26 to wet the filter before the anticoagulated whole blood reaches the filter. Once wetted, the microprocessor closes blood line clamp 24 and opens reinfusion line clamp 48 to prime reservoir 42.

The system affords assurance that the initial charge of anticoagulant has contacted and wetted the filter. This may be provided by a signal, for example, generated by a predetermined number of turns of the blood pump. The tube run 12 is such that the charge of anticoagulant will have reached and wetted the filter before the blood pump has made the predetermined number of turns and before generation of the signal in response thereto. In response to the signal, the microprocessor closes blood line clamp 24 and opens reinfusion line clamp 48. Consequently, a predetermined quantity or charge of anticoagulant is provided through blood line 12 to wet the separation filter in advance of the anticoagulated whole blood and prior to priming the reservoir.

After the filter is wetted, blood line clamp 24 closes and reinfusion line clamp 48 opens as previously described whereby blood is diverted into reinfusion line 46 to prime reservoir 42. When in the reservoir priming mode, anticoagulated whole blood is pumped by pump 22 from the donor through reinfusion line 46 and into reservoir 42. Once this priming action is completed, clamps 24 and 48 are opened and closed, respectively, whereby the first collection cycle begins with anticoagulated whole blood flowing through blood line 12 into separation device 26 and to the previously wetted filter.

In this manner, the first fluid that enters the separation device during the first collection cycle is the initial charge of anticoagulant. This charge of anticoagulant wets the filter. A portion of this initial charge of coagulant flows from the separator to the reinfusion reservoir 42 for infusion into the donor in the following or first reinfusion cycle. Another portion flows into the plasma collection bag. It will be appreciated that immediately behind this charge of anticoagulant is whole blood flowing from the donor and mixed with anticoagulant from line 14. This anticoagulated whole blood then flows into separation device 26 for separation into plasma and cell concentrate.

The operation of the instrument continues this first collection cycle. That is, the separated plasma flows from separation device 26 through plasma line 34 into plasma collection container 36. The concentrated cells flow through line 40 by the action of pump 44 into reservoir 42 until the latter is substantially filled. In the first collection cycle, a portion of the predetermined quantity of anticoagulant used to wet the filter is collected in the reservoir 42 together with the separated cell concentrate. Once the reservoir 42 is full, the collection cycle ceases and the reinfusion cycle commences. That is, reinfusion line clamp 48 is opened and blood line clamp 24 is closed. Blood pump 22 is then operated in reverse to pump the combined cell concentrate and anticoagulant portion of the initial anticoagulant charge from reservoir 42 through lines 46 and 22 back to the donor through the phlebotomy needle set 10. The reinfusion cycle ends when the reinfusion reservoir 42 has been emptied and its contents returned to the donor. Thus, only a very small quantity of anticoagulant corresponding to a portion of the initial charge of anticoagulant necessary for wetting the filter is provided the donor during the first reinfusion cycle. For example, the instrument setting and tube runs are designed to minimize and therefore provide only a small portion of the initial charge of anticoagulant, for example, about 3 to 4 ml, and preferably no more than 5 ml, for flow into the reservoir and subsequent infusion into the donor.

The microprocessor then controls the instrument to advance to the next collection cycle. In this subsequent collection cycle, it will be appreciated that anticoagulated blood flows through the blood line 12 by operation of blood pump 22 to separation device 26 without being preceded by a charge of anticoagulant inasmuch as the filter has been previously wetted during start-up. The collection and reinfusion cycles are alternated until the designated quantity of plasma has been collected.

At the end of the procedure, the system is purged of blood products. In this connection, it will be appreciated that an air vent, not shown, is provided in the reservoir 42 to assist the system when purging blood at the end of the procedure for return to the donor. The air vent additionally assists during the reinfusion cycles to avoid creation of undesirable pressures in the system.

While the preferred embodiment hereof does not require a saline line, such line may be provided, as indicated by the dashed line 28 in FIG. 1. A breathable sterility protector 30 may be provided at the end spike of such line 28. Line 28 may be connected to the anticoagulant supply for initially wetting the filter (in substitution for certain of the steps outlined above) although, after wetting, such line should be clamped to avoid inadvertent and undesirable addition of excess anticoagulant.

Consequently, it will be appreciated that the objects of the present invention have been fully accomplished in that there has been provided a method for wetting a plasmapheresis filter with anticoagulant in a plasmapheresis system wherein the filter is first wetted by a very small quantity of anticoagulant which is insufficient to adversely affect the donor but which wetting is necessary to avoid hemolysis of the initial blood portion, high initial transfilter pressures, and subsequent plugging of the filter.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of wetting a plasmapheresis filter with anticoagulant in a plasmapheresis system having a venepuncture needle and a plasma separation device including a plasmapheresis filter, the needle and separation device being connected by a fluid conduit, comprising the steps of:
   providing said conduit with a predetermined amount of anticoagulant of insufficient quantity in said conduit to reach the separation device;
   performing the venepuncture to provide the conduit with whole blood from a donor; and
   pumping the whole blood in said conduit to advance the predetermined amount of anticoagulant along said conduit such that the predetermined amount of anticoagulant is provided said separation device first and in advance of the whole blood to wet the plasmapheresis filter before the whole blood contacts the filter.

2. A method according to claim 1 wherein the system includes a blood pump between the venepuncture needle and the separation device, and including the further step of providing the anticoagulant at a location between the venepuncture needle and the blood pump.

3. A method according to claim 1 including pumping a predetermined amount of anticoagulant into said conduit, detecting the presence of said predetermined amount of anticoagulant in said conduit, providing a signal in response to said detection and discontinuing the pumping of anticoagulant in response to said signal and prior to performing the venepuncture.

4. A method according to claim 3 wherein the last four steps of pumping, detecting, providing and discontinuing pumping are performed prior to performing venepuncture.

5. A method according to claim 3 wherein the system includes a reservoir for collecting and reinfusing cell concentrate and including the further step of providing anticoagulated whole blood to the reservoir to prime the latter.

6. A method according to claim 1 including flowing a portion of the predetermined amount of anticoagulant into the reservoir from the separation device, said anticoagulant portion being less than about 5 ml.

7. A method according to claim 1 wherein said predetermined amount comprises solely anticoagulant.

8. A method of wetting a plasmapheresis filter with anticoagulant in a plasmapheresis system having a venepuncture needle and a plasma separation device including a plasmapheresis filter, the needle and separation device lying in communication with one another, comprising the steps of:
   providing the system between the needle and the separation device with an initial charge of anticoagulant of insufficient quantity for flow to the separation device;
   performing the venepuncture to provide the system with whole blood from the donor for flow to the separation device; and
   operating the system such that the initial charge of anticoagulant flows immediately ahead of the flow of whole blood so that the anticoagulant wets the filter of the separation device before the whole blood from the donor flows to the separation device.

9. A method according to claim 8 wherein the step of performing venepuncture is accomplished before the system is operated to wet the filter.

10. A method according to claim 8 including pumping a predetermined amount of anticoagulant into said system, detecting the presence of said predetermined amount of anticoagulant in said system, providing a signal in response to said detection and discontinuing the pumping of anticoagulant in response to said signal and prior to performing the venepuncture.

11. A method according to claim 10 wherein the last four steps of pumping, detecting, providing and discontinuing pumping are performed prior to performing venepuncture.

12. A method according to claim 10 wherein the system includes a reservoir for collecting and reinfusing cell concentrate and including the further step of providing anticoagulated whole blood to the reservoir to prime the latter.

13. A method according to claim 8 wherein the system includes a reservoir for containing cell concentrate separated by the separation device, including the further step of flowing at least a portion of the initial charge of anticoagulant into said reservoir from (the separation device) after the filter is wetted thereby.

14. A method according to claim 13 including operating the system to flow the cell concentrate and the initial charge of anticoagulant in the reservoir to the blood donor.

15. A method according to claim 8 wherein said initial charge comprises solely anticoagulant.

16. A method of wetting a plasmapheresis filter with anticoagulant in a plasmapheresis system having a venepuncture needle and a plasma separation device connected by a fluid conduit, comprising the steps of:
   pumping a predetermined amount of anticoagulant into said conduit, detecting the presence of said predetermined amount of anticoagulant in said conduit, providing a signal in response to said detection and discontinuing the pumping of anticoagulant in response to said signal and prior to performing venepuncture;

performing the venepuncture to provide the conduit with whole blood from a donor;

pumping the whole blood in said conduit such that the predetermined amount of anticoagulant in said conduit is provided said separation device first and in advance of the whole blood to wet the plasmapheresis filter before the whole blood contacts the filter; and the steps of pumping, detecting and discontinuing pumping being performed prior to performing venepuncture and, subsequent to venepuncture, the further steps of detecting the presence of a predetermined amount of anticoagulant and whole blood in said conduit sufficient such that the predetermined amount of anticoagulant has reached the filter and providing a signal in response thereto, and diverting whole blood to a cell concentrate and reinfusing reservoir to prime the latter.

17. A method of wetting a plasmapheresis filter with anticoagulant in a plasmapheresis system having a venepuncture needle and a plasma separation device, comprising the steps of:

pumping a predetermined amount of anticoagulant into said system, detecting the presence of said predetermined amount of anticoagulant in said system, providing a signal in response to said detection and discontinuing the pumping of anticoagulant in response to said signal and prior to performing venepuncture;

performing the venepuncture to provide the system with whole blood from the donor for flow to the separation device; and operating the system such that the initial charge of anticoagulant wets the filter of the separation device before the whole blood from the donor flows to the separation device;

the steps of pumping, detecting and discontinuing pumping being performed prior to performing venepuncture and, subsequent to venepuncture, the further steps of detecting the presence of a predetermined amount of anticoagulant and whole blood in said system sufficient such that the predetermined amount of anticoagulant has reached the filter and providing a signal in response thereto, and diverting whole blood to a cell concentrate and reinfusing reservoir to prime the latter.

* * * * *